United States Patent
Bauer et al.

(10) Patent No.: US 9,321,986 B2
(45) Date of Patent: *Apr. 26, 2016

(54) COMBINATIONS OF 1-AZA-3,7-DIOXABICYCLO[3.3.0]OCTANE COMPOUNDS AND SILICIC ACID ESTERS AND THE USE OF SAME AS PRO-FRAGRANCES

(71) Applicant: Henkel AG & Co. KGaA, Duesseldorf (DE)

(72) Inventors: Andreas Bauer, Kaarst (DE); Ursula Huchel, Cologne (DE); Andreas Gerigk, Erkelenz (DE); Marc Weyhe, Krefeld (DE); Thomas Gerke, Duesseldorf (DE); Hubert Smyrek, Krefeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/333,833

(22) Filed: Jul. 17, 2014

(65) Prior Publication Data

US 2014/0329732 A1    Nov. 6, 2014

Related U.S. Application Data

(63) Continuation of application No. PCT/EP2012/075717, filed on Dec. 17, 2012.

(30) Foreign Application Priority Data

Feb. 1, 2012 (DE) .................... 10 2012 201 424

(51) Int. Cl.

| | | |
|---|---|---|
| *C11D 3/50* | (2006.01) |
| *A61K 8/49* | (2006.01) |
| *A61K 8/58* | (2006.01) |
| *A61Q 13/00* | (2006.01) |
| *C11D 3/00* | (2006.01) |
| *C11D 3/16* | (2006.01) |
| *A61Q 5/02* | (2006.01) |
| *A61Q 19/10* | (2006.01) |

(52) U.S. Cl.
CPC . *C11D 3/502* (2013.01); *A61K 8/49* (2013.01); *A61K 8/585* (2013.01); *A61Q 13/00* (2013.01); *C11D 3/0068* (2013.01); *C11D 3/162* (2013.01); *C11D 3/507* (2013.01); *A61Q 5/02* (2013.01); *A61Q 19/10* (2013.01)

(58) Field of Classification Search
CPC ....................................................... C11D 3/507
USPC .................................................. 510/103, 104
See application file for complete search history.

(56) References Cited

U.S. PATENT DOCUMENTS

| | | |
|---|---|---|
| 4,277,353 A | 7/1981 | Deen et al. |
| 6,861,402 B1 | 3/2005 | Miracle et al. |
| 2004/0072704 A1* | 4/2004 | Gerke .................... A61K 8/585 510/101 |
| 2005/0256313 A1 | 11/2005 | Norenberg et al. |
| 2008/0305063 A1 | 12/2008 | Huchel et al. |
| 2009/0312231 A1 | 12/2009 | Huchel et al. |

FOREIGN PATENT DOCUMENTS

WO        00/14091 A1    3/2000

OTHER PUBLICATIONS

PCT International Search Report (PCT/EP2012/075717) dated May 4, 2013.

* cited by examiner

*Primary Examiner* — John Hardee
(74) *Attorney, Agent, or Firm* — P. Scott Smith

(57) ABSTRACT

The invention relates to combinations of 1-aza-3,7-dioxabicyclo[3.3.0]octane compounds with silicic acid esters, methods for producing same, the use of same as pro-fragrances, as well as washing and cleaning agents, fabric softeners and cosmetics that contain same. The invention also relates to a method for prolonging the perception of fragrance in such agents.

13 Claims, No Drawings

COMBINATIONS OF 1-AZA-3,7-DIOXABICYCLO[3.3.0]OCTANE COMPOUNDS AND SILICIC ACID ESTERS AND THE USE OF SAME AS PRO-FRAGRANCES

FIELD OF THE INVENTION

The present invention generally relates to combinations of 1-aza-3,7-dioxabicyclo[3.3.0]octane compounds with silicic acid esters, to the use thereof as pro-scents and to washing and cleaning agents, fabric softeners, and cosmetics containing them, and to methods for extending the scent sensation of such agents and for counteracting bad odors.

BACKGROUND OF THE INVENTION

Besides the direct addition of scents to washing and cleaning agents, fabric softeners, and cosmetics, the addition of so-called pro-scents has also been proposed. Pro-scents, analogously to pro-drugs, represent a chemical derivative of a scent which, for example, decreases the volatility of the scent and permits a time-delayed release of the scent under ambient conditions. By derivatizing scents such as scent aldehydes, scent ketones, or scent alcohols, it is possible to lower the vapor pressure of these compounds. Because the derivatization reaction is reversible, the chemically bound scent aldehyde, scent ketone, or scent alcohol can be cleaved at the binding site under specific conditions, for example ambient conditions. The scent aldehyde or scent ketone is thereby released again; this can result in an extended scent impression.

In addition, besides extending the scent impression, counteracting bad odors also plays a large role.

U.S. Pat. No. 6,861,402 describes pro-scents that contain a scent aldehyde or scent ketone bound in the form of an oxazolidine. For example, N-benzylethanolamine is reacted with a scent in order to yield a monocyclic oxazolidine.

WO 2004/009564 A2 relates to cyclic co-surfactants that are produced by a condensation reaction of $C_3$ to $C_6$ aldehydes with polyvalent alcohols, amines, thiols, or carboxylic acids. The co-surfactants are suitable for use in household washing agents, household cleaners, body cleansing agents, and toiletries.

The object of the present invention is thus to furnish improved scent precursor forms, so-called pro-scents, that can sustainably cover bad odors even over a period of several days.

The term "bad odor" is commonly known to one skilled in the art. A "bad odor" for purposes of this Application includes all odors that, in a group of ten persons, is categorized by at least seven of those persons as unpleasant or bad. Examples of such bad odors are perspiration odor, fecal odor, mildew odor, bacterially generated bad odor, fish odor, the odor of $C_1$ to $C_{15}$ fatty acids, or the odor of wet laundry that has stood for hours.

The object of the present invention is furthermore to furnish pro-scents that permit an extended scent impression in the context of scent aldehydes, scent ketones, and scent alcohols that inherently have a high vapor pressure. A further intention is to obtain a pleasant and long-lasting scent with the substrates treated with the compounds according to the present invention.

The object in particular was to furnish hydrolysis-stable pro-scents that can be incorporated into aqueous compositions, for example into aqueous washing and cleaning agents, and that result in a positive scent impression on the user even several days after utilization and in the presence of bad odors, for example from wet, washed laundry that has been left for several days in the washing machine or laundry basket.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A combination of (a) a 1-aza-3,7-dioxabicyclo[3.3.0]octane compound of the general formula (I)

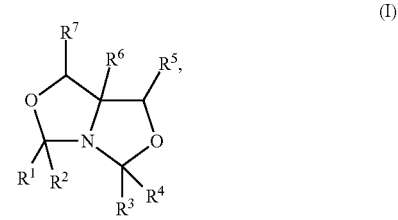

(I)

wherein $R^1$, $R^2$, $R^3$, $R^4$ mutually independently denote residues that, in a compound of the general formula $R^1$—C(=O)—$R^2$ or $R^3$—C(=O)—$R^4$, yield a scent aldehyde having at least six carbon atoms or a scent ketone having at least six carbon atoms, $R^5$, $R^6$, $R^7$ mutually independently denote H or a hydrocarbon residue that can be acyclic or cyclic, substituted or unsubstituted, branched or unbranched as well as saturated or unsaturated, or mixtures of said compounds; and (b) a silicic acid ester of the general formula (II)

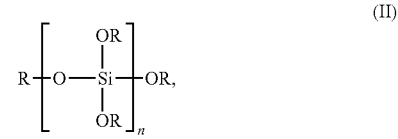

(II)

wherein n assumes values in the range from 2 to 100, and all R are selected mutually independently from the group of hydrogen, straight-chain or branched, saturated or unsaturated, substituted or unsubstituted $C_{1-6}$ hydrocarbon residues and scent alcohol residues, with the provision that at least one R denotes a scent alcohol residue, or mixtures of said compounds.

A method for degrading bad odors by using a combination of (a) a 1-aza-3,7-dioxabicyclo[3.3.0]octane compound of the general formula (I)

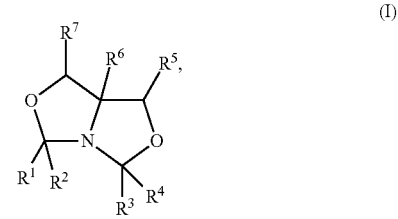

(I)

wherein $R^1$, $R^2$, $R^3$, $R^4$ mutually independently denote residues that, in a compound of the general formula $R^1$—C(=O)—$R^2$ or $R^3$—C(=O)—$R^4$, yield a scent aldehyde having at least six carbon atoms or a scent ketone having at least six carbon atoms, $R^5$, $R^6$, $R^7$ mutually independently denote H or a hydrocarbon residue that can be acyclic or cyclic, substituted or unsubstituted, branched or unbranched as well as saturated or unsaturated, or mixtures of said compounds, and (b) a silicic acid ester of the general formula (II)

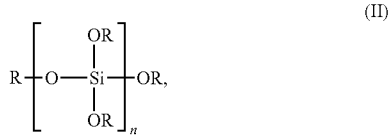

wherein n assumes values in the range from 2 to 100, and all R are selected mutually independently from the group of hydrogen, straight-chain or branched, saturated or unsaturated, substituted or unsubstituted $C_{1-6}$ hydrocarbon residues and scent alcohol residues, with the provision that at least one R denotes a scent alcohol residue, or mixtures of said compounds.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found, surprisingly, that combinations of scent aldehydes and/or scent ketones that are present in a manner derivatized as 1-aza-3,7-dioxabicyclo[3.3.0]octane compounds (bicyclic oxazolidine derivatives), with scent alcohols that are present in a manner derivatized as silicic acid esters, exhibit synergistic properties in terms of counteracting and covering bad odors, in particular over a period of several days.

The object is therefore achieved by a combination of
(a) a 1-aza-3,7-dioxabicyclo[3.3.0]octane compound of the general formula (I)

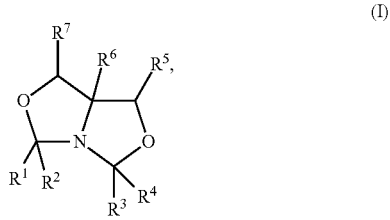

wherein
$R^1$, $R^2$, $R^3$, $R^4$ mutually independently denote residues that, in a compound of the general formula $R^1$—C(═O)—$R^2$ or $R^3$—C(═O)—$R^4$, yield a scent aldehyde having at least six carbon atoms or a scent ketone having at least six carbon atoms,
$R^5$, $R^6$, $R^7$ mutually independently denote H or a hydrocarbon residue that can be acyclic or cyclic, substituted or unsubstituted, branched or unbranched as well as saturated or unsaturated,
or mixtures of said compounds, and
(b) a silicic acid ester of the general formula (II)

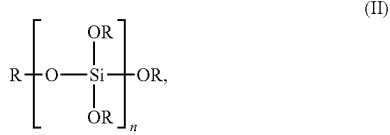

wherein
n assumes values in the range from 2 to 100, and
all R are selected mutually independently from the group of hydrogen, straight-chain or branched, saturated or unsaturated, substituted or unsubstituted $C_{1-6}$ hydrocarbon residues and scent alcohol residues, with the provision that at least one R denotes a scent alcohol residue, or mixtures of said compounds.

It is preferred to use, in the combinations according to the present invention, those compounds of the general formula (I) in which $R^1$, $R^2$, $R^3$, $R^4$ mutually independently denote residues that, in a compound of the general formula $R^1$—C(═O)—$R^2$ or $R^3$—C(═O)—$R^4$, respectively yield a scent aldehyde having at least 6 carbon atoms.

In a particular embodiment of the present invention, it is preferred to use in the combinations according to the present invention those compounds of the general formula (I) in which residues $R^1$ and $R^2$ or $R^3$ and $R^4$ that yield a scent ketone in a compound of the general formula $R^1$—C(═O)—$R^2$ or $R^3$—C(═O)—$R^4$, respectively, are present at most in one of the structural elements —$CR^1R^2$ or —$CR^3R^4$, respectively.

Preferred residues $R^6$ are methyl, ethyl, and hydroxymethyl residues. $R^5$ and $R^7$ are preferably hydrogen or a $C_{1-6}$ alkyl residue, preferably a $C_{1-3}$ alkyl residue. Particularly preferably, $R^5$ and $R^7$ are hydrogen or a methyl or ethyl residue, in particular hydrogen.

In particularly preferred compounds of the general formula (I), $R^2$, $R^4$, $R^5$, $R^6$, $R^7$ signify hydrogen, and $R^1$ and $R^3$ each signify a $C_{5-24}$ hydrocarbon residue.

It is preferred to use, in the combinations according to the present invention, those compounds of the general formula (I) in which the residues R', $R^2$, $R^3$ and $R^4$ yield, in a compound of the general formula $R^1$—C(═O)—$R^2$ or $R^3$—C(═O)—$R^4$, a scent aldehyde or a scent ketone that is selected from the list made up of jasmones; ionones, damascones and damascenones, menthone, carvone, Iso-E-Super, methylheptenone, melonal; cymal; ethylvanillin, helional; hydroxycitronellal; koavone; methyl nonyl acetaldehyde; phenylacetaldehyde; undecylenealdehyde; 3-dodecen-1-al, alpha-n-amylcinnamaldehyde, benzaldehyde, 3-(4-tert-butylphenyl)propanal, 2-methyl-3-(para-methoxyphenylpropanal), 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 2,4-dimethyl-3-cyclohexene-1-carboxyaldehyde, 2-methyl-3-(isopropylphenyl)propanal, decylaldehyde, 2,6-dimethyl-5-heptenal; alpha-n-hexylcinnamaldehyde, 7-hydroxy-3,7-dimethyloctanal, undecenal, 2,4,6-trimethyl-3-cyclohexene-1-carboxaldehyde, 1-dodecanal, 2,4-dimethylcyclohexene-3-carboxaldehyde, 4-(4-hydroxy-4-methylpentyl)-3-cylohexene-1-carboxaldehyde, 2-methylundecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 3,7-dimethyloctan-1-al, 1-undecanal, 10-undecen-1-al, 4-hydroxy-3-methoxybenzaldehyde, trans-4-decenal, 2,6-nonadienal, para-tolylacetaldehyde, 3,7-dimethyl-2-methylene-6-octenal, 2-methyloctanal, alpha-methyl-4-(1-methylethyl)benzeneacetaldehyde, 2-methyl-3-phenyl-2-propen-1-al, 3,5,5-trimethylhexanal, 3-propylbicyclo[2.2.1]hept-5-ene-2-carbaldehyde, 9-decenal, 3-methyl-5-phenyl-1-pentanal, methyl nonyl acetaldehyde, citral, 1-decanal, florhydral, 2,4-dimethyl-3-cyclohexene-1-carboxaldehyde, and/or heliotropin. These scent aldehydes and/or scent ketones yield particularly good results in terms of counteracting and covering bad odors.

It is preferred to use, in the combinations according to the present invention, those silicic acid ester of the general formula (II) in which at least 10 mol %, preferably at least 20 mol % and particularly preferably even more than 40 mol % of the residues R are scent alcohol residues. It is particularly preferred if these scent alcohols residues are selected from the group of the residues of the following scent alcohols: 10-undecen-1-ol, 2,6-dimethylheptan-2-ol, 2-methylbutanol, 2-methylpentanol, 2-phenoxyethanol, 2-phenylpropanol, 2-tert-butylcyclohexanol, 3,5,5-trimethylcyclohexanol, 3-hexanol, 3-methyl-5-phenylpentanol, 3-octanol, 3-phenylpropanol, 4-heptenol, 4-isopropylcyclohexanol, 4-tert-butylcyclohexanol, 6,8-dimethyl-2-nonanol, 6-nonen-1-ol, 9-decen-1-ol, α-methylbenzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethylbenzylcarbinol, dimethylheptanol, dimethyloctanol, ethyl salicylate, ethylvanillin, eugenol, farnesol, geraniol, heptanol, hexyl salicylate, isoborneol, isoeugenol, isopulegol, linalool, menthol, myrtenol, n-hexanol, nerol, nonanol, octanol, p-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, champiniol, hexenol, and/or cinnamyl alcohol. These scent alcohols yield particularly good results in terms of counteracting and covering bad odors.

Particularly outstanding results in terms of counteracting and covering bad odors have been obtained with the use of compounds of the general formula (I) with residues that yield one of the aforementioned preferred scent aldehydes and/or scent ketones in combination with a silicic acid ester of the general formula (II) with residues that yield one of the aforementioned preferred scent alcohols.

The combinations according to the present invention of compounds of the general formulas (I) and (II) can furthermore contain mixtures having compounds of the general formula (III)

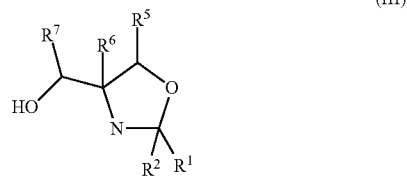

(III)

wherein
$R^1$, $R^2$ mutually independently denote residues that, in a compound of the general formula $R^1$—C(=O)—$R^2$, yield a scent aldehyde having at least six carbon atoms or a scent ketone having at least six carbon atoms,
$R^5$, $R^6$, $R^7$ mutually independently denote H or a hydrocarbon residue that can be acyclic or cyclic, substituted or unsubstituted, branched or unbranched as well as saturated or unsaturated,
or mixtures of said compounds.

A further subject of the present invention is the use of the combinations according to the present invention of the compound of the general formulas (I) and (II) or mixtures thereof, with compounds of the general formula (III), as pro-scents. The pro-scents according to the present invention preferably gradually release, by hydrolysis, the scents derivatized therein.

The compounds and agents according to the present invention exhibit good hydrolytic cleavability under ambient conditions. They furthermore exhibit good shelf stability in an alkaline environment such as the one encountered, for example, in washing agents and dishwashing agents.

Because of the outstanding suitability of the compounds according to the present invention for use in washing and cleaning agents, utilization of the pro-scents according to the present invention in liquid or solid washing and cleaning agents, particularly preferably as a scent, is a further subject of the present invention.

The pro-scents according to the present invention are likewise outstandingly suitable for use in cosmetics (cosmetic agents); a further subject of the present invention is therefore use of the pro-scents according to the present invention in cosmetics (cosmetic agents) for skin and hair treatment, particularly preferably as a scent.

In a particular embodiment, the claimed combinations release scent aldehyde and scent alcohols as scents. In a further particular embodiment, the claimed combinations release scent aldehydes, scent ketones, and scent alcohols as scents. The combinations according to the present invention are preferably employed together with other scents.

The combinations according to the present invention of the compound of the general formulas (I) and (II) or mixtures thereof, with compounds of the general formula (III), are contained in the agents, preferably washing or cleaning agents, fabric softeners, or cosmetics, in quantities of less than 5 wt %, preferably less than 2 wt %, in particular less than 1 wt %, based in each case on the total quantity of the agents.

A further subject of the present invention is a method for extending the scent sensation of agents, preferably washing or cleaning agents, fabric softeners, or cosmetics, or of solid surfaces treated therewith, wherein combinations of the compound of the general formulas (I) and (II) or mixtures thereof, with compounds of the general formula (III), are added to the agents, preferably washing or cleaning agents, fabric softeners, or cosmetics. The scents are preferably released again by hydrolysis.

A method for degrading bad odors by using a combination of
(a) a 1-aza-3,7-dioxabicyclo[3.3.0]octane compound of the general formula (I)

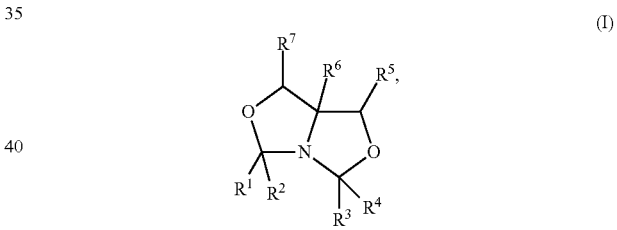

(I)

wherein
$R^1$, $R^2$, $R^3$, $R^4$ mutually independently denote residues that, in a compound of the general formula $R^1$—C(=O)—$R^2$ or $R^3$—C(=O)—$R^4$, yield a scent aldehyde having at least six carbon atoms or a scent ketone having at least six carbon atoms,
$R^5$, $R^6$, $R^7$ mutually independently denote H or a hydrocarbon residue that can be acyclic or cyclic, substituted or unsubstituted, branched or unbranched as well as saturated or unsaturated,
or mixtures of said compounds, and
(b) a silicic acid ester of the general formula (II)

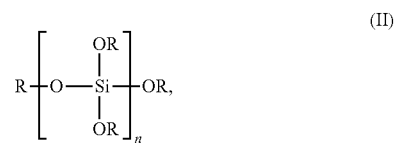

(II)

wherein
n assumes values in the range from 2 to 100, and
all R are selected mutually independently from the group of hydrogen, straight-chain or branched, saturated or unsaturated, substituted or unsubstituted $C_{1-6}$ hydrocarbon residues and scent alcohol residues, with the provision that at least one R denotes a scent alcohol residue, or mixtures of said compounds.

Oil-soluble substituted mono- and bicyclic oxazolidines that are employed as additives, for example, in automatic transmission fluids, are known from U.S. Pat. No. 4,277,353. Reaction products of optionally substituted 2-amino-1,3-propanediols with paraformaldehyde and isobutyraldehyde are described by way of example. The derivatization of scent aldehydes or scent ketones is not mentioned, however. According to an embodiment of the present invention, the following compounds are excepted: 1-aza-3,7-dioxa-5-methylbicyclo[3.3.0]octane, 1-aza-3,7-dioxa-5-ethylbicyclo[3.3.0]octane, 1-aza-3,7-dioxabicyclo[3.3.0]octane, and 1-aza-3,7-dioxa-2,8-diisopropyl-5-ethylbicyclo[3.3.0]octane. In addition, according to an embodiment of the present invention $R^1$ and $R^3$ are not $C_{1-30}$ hydrocarbyl residues provided $R^2$ and $R^4$ and $R^5$ and $R^7$ are hydrogen and $R^6$ signifies hydrogen, methyl, or ethyl. Also excluded according to an embodiment of the invention are compounds in which, in the structural element —$CR^1R^2$, the residue $R^1$ is a $C_{1-30}$ hydrocarbyl residue and $R^2$ is hydrogen, and in the structural element —$CR^3R^4$, the residues $R^3$ and $R^4$ each represent $C_{1-7}$ hydrocarbyl residues.

"Scent aldehydes," "scent ketones," or "scent alcohols" are understood for purposes of this Application as all fragrances and scents of the chemical substance classes of the aldehydes, ketones, or alcohols that are typically employed to bring about a pleasant scent perception.

Scent aldehydes and/or scent ketones that are reacted with 2-amino-1,3-propanediols, and derivatives thereof, are present in the compounds of the general formula (I). The scent ketones can comprise all ketones that can impart a desired scent or a fresh impression. Mixtures of different ketones can also be employed. The ketone can be selected, for example, from the group consisting of Buccoxime, isojasmone, methyl beta-naphthyl ketone, musk indanone, Tonalid/Musk plus, alpha-damascone, beta-damascone, delta-damascone, isodamascone, damascenone, damarose, methyldihydrojasmonate, menthone, carvone, camphor, fenchone, alpha-ionone, beta-ionone, gamma-methyl (so-called) ionone, fleuramone, dihydrojasmone, cis-jasmone, Iso-E-Super, methyl cedrenyl ketone or methyl cedrylone, acetophenone, methylacetophenone, para-methoxyacetophenone, methyl beta-naphthyl ketone, benzylacetone, benzophenone, para-hydroxyphenylbutanone, celery ketone or livescone, 6-isopropyldecahydro-2-naphthone, dimethyloctenone, frescomenthe, 4-(1-ethoxyvinyl)-3,3,5,5-tetramethylcyclohexanone, methylheptenone, 2-(2-(4-methyl-3-cyclohexen-1-yl)propyl)cyclopentanone, 1-(p-menthen-6(2)yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4 (5H)indanone, 4-damascol, dulcinyl or cassione, gelsone, hexylone, isocyclemone E, methylcyclocitrone, methyl lavender ketone, orivone, para-tert-butylcyclohexanone, verdone, delphone, muscone, neobutenone, plicatone, veloutone, 2,4,4,7-tetramethyloct-6-en-3-one, tetrameran, hedione, and mixtures thereof. The ketones can preferably be selected from alpha-damascone, delta-damascone, isodamascone, carvone, gamma-methyl ionone, Iso-E-Super, 2,4,4,7-tetramethyloct-6-en-3-one, benzylacetone, beta-damascone, damascenone, methyl dihydrojasmonate, methyl cedrylone, hedione, and mixtures thereof.

Suitable scent aldehydes can be any aldehydes that, analogously to the scent ketones, produce a desired scent or a fresh impression. These can again be individual aldehydes or aldehyde mixtures. Suitable aldehydes are, for example, melonal, triplal, ligustral, adoxal, anisaldehyde, cymal, ethylvanillin, florhydral, helional, heliotropin, hydroxycitronellal, koavone, lauryl aldehyde, lyral, methyl nonyl acetaldehyde, p,t-bucinal, phenyl acetaldehyde, undecylene aldehyde, vanillin, 2,6,10-trimethyl-9-undecenal, 3-dodecen-1-al, alpha-n-amylcinnamaldehyde, 4-methoxybenzaldehyde, benzaldehyde, 3-(4-tert-butylphenyl)propanal, 2-methyl-3-(para-methoxyphenylpropanal), 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyl aldehyde, 1,2,3,4,5,6,7,8-octahydro-8,8-dimethyl-2-naphthaldehyde, 2,4-dimethyl-3-cyclohexene-1-carboxyaldehyde, 2-methyl-3-(isopropylphenyl)propanal, decyl aldehyde, 2,6-dimethyl-5-heptenal, 4-(tricyclo[5.2.1.0(2,6)]-decylidene-8) butanal, octahydro-4,7-methano-1H-indenecarboxaldehyde, 3-ethoxy-4-hydroxybenzaldehyde, para-ethyl-alpha,alpha-dimethylhydrocinnamaldehyde, alpha-methyl-3,4-(methylenedioxy)hydrocinnamaldehyde, 3,4-methylenedioxybenzaldehyde, alpha-n-hexylcinnamaldehyde, m-cymene-7-carboxaldehyde, alpha-methyl phenyl acetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexene carboxaldehyde, 1-dodecanal, 2,4-dimethylcyclohexene-3-carboxaldehyde, 4-(4-hydroxy-4-methylpentyl-3-cyclohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 1-methyl-4-(4-methyl-3-pentenyl)-3-cyclohexene-1-carboxaldehyde, 5- or 6-methoxyhexahydro-4,7-methanoindane-1- or 2-carboxyaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexene carboxyaldehyde, 7-hydroxy-3,7-dimethyloctanal, trans-4-decenal, 2,6-nonadienal, para-tolylacetaldehyde, 4-methyl phenyl acetaldehyde, 2-methyl-4-(2,6,6-trimethyl-1-cyclohexen-1-yl)-2-butenal, ortho-methoxycinnamaldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindane-1-carboxaldehyde, 2-methyloctanal, alpha-methyl-4-(1-methylethyebenzeneacetaldehyde, 6,6-dimethyl-2-norpinene-2-propionaldehyde, para-methylphenoxyacetaldehyde; 2-methyl-3-phenyl-2-propen-1-al, 3,5,5-trimethylhexanal, hexahydro-8,8-dimethyl-2-naphthaldehyde, 3-propylbicyclo[2.2.1]hept-5-ene-2-carbaldehyde, 9-decenal, 3-methyl-5-phenyl-1-pentanal, methyl nonyl acetaldehyde, 1-p-menthene-q-carboxaldehyde, citral, or mixtures thereof, lilial, citral, 1-decanal, florhydral, 2,4-dimethyl-3-cyclohexene-1-carboxaldehyde. Preferred aldehydes can be selected from cis/trans-3,7-dimethyl-2,6-octadien-1-al, heliotropin, 2,4,6-trimethyl-3-cyclohexene-1-carboxaldehyde, 2,6-nonadienal, alpha-n-amylcinnamaldehyde, alpha-n-hexylcinnamaldehyde, p-tert-bucinal, lyral, cymal, methyl nonyl acetaldehyde, trans-2-nonenal, lilial, trans-2-nonenal, and mixtures thereof.

As stated above by way of example, the scent aldehydes and scent ketones can have an aliphatic, cycloaliphatic, aromatic, ethylenically unsaturated structure, or a combination of those structures. Further heteroatoms or polycyclic structures can also be present. The structures can have suitable substituents such as hydroxyl or amino groups.

The combination furthermore contains, by way of the compounds of the general formula (I), a scent aldehyde and/or a scent ketone. This means that the combination can contain only one type of scent aldehyde or only one type of scent ketone. Also encompassed thereby, however, is the fact that the combination can contain one type of scent aldehyde and one type of scent ketone. Also encompassed is the fact that the combination can contain several types of scent aldehyde or several types of scent ketone. It is likewise possible for the combination to contain several types of scent aldehyde and one type of scent ketone, or several types of scent aldehyde and several types of scent ketone. In a further embodiment, the combination contains several types of scent ketone and one type of scent aldehyde, or several types of scent ketone and several types of scent aldehydes.

Scent alcohols that are reacted with silicic acids, and derivatives thereof, are present in the compounds of the general formula (II).

Oligosilicic acid esters of lower alcohols are commercially obtainable; methanol, ethanol, n-propanol, isopropanol, n-butanol, isobutanol, and tert-butanol have usually been used for esterification. The preparation of oligosilicic acid esters not completely transesterified with scent alcohols results in silicic acid ester mixtures in which some of the residues R are selected from the group of methyl, ethyl, n-propyl, isopropyl, n-butyl, isobutyl, and tert-butyl. Such compounds are preferred in the context of the present invention.

Those oligosilicic acid esters which contain at least one residue R from the group of scent alcohol residues are.

The compounds recited are manufactured by simple transesterification of oligosilicic acid esters of lower alcohols with scent alcohols, wherein both individual scent alcohols and scent alcohol mixtures can be used. Depending on the reaction time and reaction conditions, the lower alcohols are cleaved off and the scent alcohols or biocide alcohols are bound, wherein the alcohols along Si—O—Si chains or rings are exchanged more easily than the terminal alcohols. The commercially usual silicic acid esters are usually utilized as educts. The ethanol ester is to be recited here in particular. Transesterification can be controlled exclusively by elevating the temperature and distilling off the volatile byproducts. It is preferred, however, if catalysts are used for transesterification. These are usually Lewis acids, preferably aluminum tetraisopropylate, titanium tetraisopropylate, silicon tetrachloride, or basic catalysts, or also preparations such as aluminum oxide with potassium fluoride. The oligomeric silicic acid esters thereby formed then comprise scent alcohol residues at least in part. Usually, however, the resulting esters also contain residues of lower alcohols. If small quantities of water or other hydrogen-acidic compounds are present in the context of manufacture of the silicic acid esters, an exchange of alcohol residues for OH groups also takes place. The silicic acid ester mixtures according to the present invention accordingly usually also contain hydrogen in part as a residue R.

The completely transesterified oligosilicic acid esters are particularly preferred in the context of the present invention. It is preferred in particular if these esters contain only a single residue R, i.e. only a single scent alcohol.

The degrees of oligomerization "n" of the silicic acid esters according to the present invention are between 2 and 100, preferably between 2 and 20. In preferred compounds, n assumes values between 2 and 15, preferably between 2 and 12, and in particular between 3 and 10, with particular preference for the values 4, 5, 6, 7, and 8.

The term "scent alcohols" is understood in the context of the present invention to mean scents that possess free hydroxyl groups and that can be esterified, regardless of the further construction of the molecule. Salicylic acid esters can therefore also be used as scent alcohols. Preferred representatives from the large group of scent alcohols can be recited, so that in the context of the present invention, silicic acid esters in which each R is selected mutually independently from the group of the residues of the following scent alcohols are preferred: 10-undecen-1-ol, 2,6-dimethylheptan-2-ol, 2-methylbutanol, 2-methylpentanol, 2-phenoxyethanol, 2-phenylpropanol, 2-tert-butylcyclohexanol, 3,5,5-trimethylcyclohexanol, 3-hexanol, 3-methyl-5-phenylpentanol, 3-octanol, 3-phenylpropanol, 4-heptenol, 4-isopropylcyclohexanol, 4-tert-butylcyclohexanol, 6,8-dimethyl-2-nonanol, 6-nonen-1-ol, 9-decen-1-ol, α-methylbenzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethylbenzylcarbinol, dimethylheptanol, dimethyloctanol, ethyl salicylate, ethylvanillin, eugenol, farnesol, geraniol, heptanol, hexyl salicylate, isoborneol, isoeugenol, isopulegol, linalool, menthol, myrtenol, n-hexanol, nerol, nonanol, octanol, para-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, cinnamyl alcohol, citronellol, eugenol, farnesol, thymol, and geraniol. Further biocide alcohols are phenoxyethanol, 1,2-propylene glycol, glycerol, citric acid and esters thereof, lactic acid and esters thereof, salicylic acid and esters thereof, 2-benzyl-4-chlorophenol, 2,2'-methylene-bis-(6-bromo-4-chlorophenol).

It is preferred to use phenylethyl silicic acid esters, geranyl silicic acid esters, citronellyl silicic acid esters, cinnamyl silicic acid esters, hexenyl silicic acid esters, nonadienyl silicic acid esters, octenyl silicic acid esters, or mixtures of two or more of these silicic acid esters.

The combinations according to the present invention of the general formulas (I) and (II) are used according to the present invention as pro-scents. The term "pro-scents" describes derivatives of scent aldehydes, of scent alcohols, and of scent ketones that, under ambient conditions, release the original scent aldehydes, scent alcohols, and scent ketones. "Ambient conditions" in this context are the typical ambient conditions in human living spaces, or the conditions to be encountered on human skin. Under ambient conditions the compounds of the general formula (I) slowly break down oppositely to the manufacturing process, releasing the original scent aldehydes and/or scent ketones. The chemically bound scent aldehydes and scent ketones are cleaved at the bonding point, thereby releasing the scents again The pro-scents according to the present invention can be employed as a single scent, but it is also possible to employ scent mixtures that are made up only in part of the pro-scent according to the present invention. It is thus possible in particular to employ scent mixtures that contain 1 to 50 wt %, preferably 5 to 40 wt %, and in particular a maximum of 30 wt % pro-scents according to the present invention, based on the total quantity of scents used comprising free scents and pro-scents. In other embodiments in which the delayed scent effect of the carrier-bound form is to be utilized in particular, in the context of the use according to the present invention advantageously at least 30 wt %, preferably at least 40 wt %, and in particular at least 50 wt % of the total perfume contained in an agent is introduced into the agent via the pro-scents according to the present invention, while the remaining 70 wt %, preferably 60 wt %, and in particular 50 wt % of the total perfume contained in the agent is sprayed onto or otherwise introduced into the agent in usual fashion. The use according to the present invention can thus advantageously be characterized in that the pro-scents according to the present invention are employed together with other scents.

The scents that can be incorporated in conventional fashion into the agents are subject to no restrictions at all. Individual scent compounds of natural or synthetic origin, for example of the ester, ether, aldehyde, ketone, alcohol, and hydrocarbon types, can thus be used as perfume oils or scents. Scent compounds of the ester type are, for example, benzyl acetate, phenoxyethyl isobutyrate, p-tert-butylcyclohexyl acetate, linalyl acetate, dimethylbenzylcarbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate, and jasmecyclate. Ethers include, for example, benzyl ethyl ether and ambroxan; aldehydes, for example, the linear alkanals having 8 to 18 carbon atoms, citral, citronellal, citronelly-loxyacetaldehyde, cyclamenaldehyde, lilial, and bourgeonal; ketones, for example, the ionones, α-isomethylionone and methyl cedryl ketone; alcohols include citronellol, eugenol, geraniol, linalool, phenylethyl alcohol, alpha-terpineol, beta-terpineol, gamma-terpineol, and delta-terpineol; and hydrocarbons include principally terpenes such as limonene and pinene. Preferably, however, mixtures of different scents that together produce an attractive scent note are used.

Perfume oils of this kind can also contain natural scent mixtures such as those accessible from plant sources, for example pine, citrus, jasmine, patchouli, rose, or ylang-ylang oil. Also suitable are muscatel sage oil, chamomile oil, clove oil, lemon balm oil, mint oil, cinnamon leaf oil, linden blossom oil, juniper berry oil, vetiver oil, olibanum oil, galbanum oil, and labdanum oil, as well as orange blossom oil, neroli oil, orange peel oil, and sandalwood oil.

Further conventional scents that are usable in the context of the present invention are, for example, the essential oils such as angelica oil, anise oil, arnica flower oil, basil oil, bay oil, champaca flower oil, silver fir oil, silver fir cone oil, elemi oil, eucalyptus oil, fennel oil, fir needle oil, galbanum oil, geranium oil, gingergrass oil, guaiac wood oil, balsam gurjun oil, helichrysum oil, ho oil, ginger oil, iris oil, cajeput oil, calamus oil, chamomile oil, camphor oil, kanaga oil, cardamom oil, cassia oil, pine needle oil, balsam copaiva oil, coriander oil, spearmint oil, caraway oil, cumin oil, lavender oil, lemon grass oil, lime oil, tangerine oil, lemon balm oil, ambrette seed oil, myrrh oil, clove oil, neroli oil, niaouli oil, olibanum oil, orange oil, oregano oil, palmarosa oil, patchouli oil, balsam peru oil, petitgrain oil, pepper oil, peppermint oil, pimento oil, pine oil, rose oil, rosemary oil, sandalwood oil, celery oil, spik oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, citron oil, and cypress oil, as well as ambrettolide, ambroxan, α-amylcinnamaldehyde, anethole, anisealdehyde, anise alcohol, anisole, anthranilic acid methyl ester, acetophenone, benzyl acetone, benzaldehyde, benzoic acid ethyl ester, benzophenone, benzyl alcohol, benzyl acetate, benzyl benzoate, benzyl formate, benzyl valerate, borneol, bornyl acetate, boisambrene forte, α-bromostyrene, n-decylaldehyde, n-dodecylaldehyde, eugenol, eugenol methyl ether, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrol, jasmone, camphor, carvacrol, carvone, p-cresol methyl ether, coumarin, p-methoxyacetophenone, methyl n-amyl ketone, methylanthranilic acid methyl ester, p-methylacetophenone, methylchavicol, p-methylquinoline, methyl β-naphthyl ketone, methyl n-nonyl acetaldehyde, methyl n-nonyl ketone, muscone, β-naphthol ethyl ether, β-naphthol methyl ether, nerol, n-nonylaldehyde, nonyl alcohol, n-octylaldehyde, p-oxyacetophenone, pentadecanolide, β-phenylethyl alcohol, phenylacetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, sandelice, skatole, terpineol, thymene, thymol, troenan, γ-undelactone, vanillin, veratrumaldehyde, cinnamaldehyde, cinnamyl alcohol, cinnamic acid, cinnamic acid ethyl ester, cinnamic acid benzyl ester, diphenyl oxide, limonene, linalool, linalyl acetate and linalyl propionate, melusate, menthol, menthone, methyl-n-heptenone, pinene, phenylacetaldehyde, terpinyl acetate, citral, citronellal, and mixtures thereof.

The pro-scents according to the present invention are employed preferably in washing and cleaning agents, fabric softeners, and cosmetics. These can be solid, gel-type, or liquid formulations; solid formulations can be present in the form of a powder, granulate, tablet, or tab. Liquid formulations can be solutions, emulsions, or dispersions.

Washing agents can serve for manual or automatic laundering of, in particular, textiles. These can be washing or cleaning agents for the industrial sector or for household use. Cleaning agents can be employed, for example, to clean hard surfaces. These can be, for example dishwashing agents that are employed for manual or automatic cleaning of dishes. They can also be usual industrial or household cleaners with which hard surfaces such as furniture surfaces, floor tiles, wall tiles, wall coverings, and floor coverings are cleaned. Fabric softeners are in particular fabric softeners that are used to treat textiles in the context of or after laundering. Cosmetics can be pastes, salves, creams, emulsions, lotions, and also solutions, in particular alcoholic solutions that are known, for example, from the fine fragrance sector. The individual agents can be applied in any desired suitable form. The agents can be, for example, ones to be applied by spraying. The pro-scents according to the present invention can furthermore be employed to cover bad odors that, for example in combination with other absorption agents, exhibit good adhesion to solid surfaces.

The invention also relates to washing or cleaning agents, fabric softeners, or cosmetics that contain the compounds or mixtures according to the present invention. The compounds or mixtures are employed in a quantity sufficient for effectiveness. Compounds of the general formula (I), or mixtures containing them are typically used in final formulations, i.e. ready-to-use washing or cleaning agents, fabric softeners, or cosmetics, in quantities of less than 5 wt %, preferably less than 2 wt %, in particular less than 1 wt %. Typical quantities contained are in the range from 0.05 to 0.5 wt %, in particular 0.1 to 0.2 wt %. In the fine fragrance sector it is also possible to work with high active-agent concentrations of up to 40 wt % scents.

Compositions of usual washing or cleaning agents, fabric softeners, and cosmetics are known to one skilled in the art. Washing and cleaning agents and fabric softeners can thus contain, besides the combinations according to the present invention of the compound of the general formula (I) and (II) or mixtures thereof, with compounds of the general formula (III), further usual ingredients of washing or cleaning agents and fabric softeners, for example surfactants, builder substances, bleaching agents, other scents, enzymes, and other active agents, but also disintegration adjuvants, so-called "tablet bursting agents," in order to facilitate the breakdown of highly compressed tablets or tabs or to shorten disintegration times.

Besides the constituents recited, the washing and cleaning agents according to the present invention can additionally contain one or more substances from the group of bleaching agents, bleach activators, enzymes, pH adjusting agents, fluorescing agents, dyes, foam inhibitors, silicone oils, anti-redeposition agents, optical brighteners, anti-gray agents, color transfer inhibitors, corrosion inhibitors, and silver protection agents.

According to the present invention, washing and cleaning agents are also dishwashing agents. The agents can in principle exhibit a variety of aggregate states. In a further preferred embodiment the fabric softeners or washing or cleaning agents are liquid or gel-type agents, in particular liquid washing agents or liquid dishwashing agents or cleaning gels; they can also, in particular, be gel-type cleaning agents for flush toilets.

The invention will be explained further by way of the Examples that follow.

EXAMPLE 1

In order to determine the degradation of bad odors, a household washing machine (Miele W1735) was loaded with 3 kg of previously worn laundry and 75 ml of a liquid heavy-duty washing agent that contained 0.45 wt % perfume (based on the total liquid washing agent). The laundry was washed at 40° C. and then left to sit for 4 days at 20° C. in the washer drum (V1).

Ten olfactorily trained persons smelled the laundry when it was fresh, after one day, and after four days, and determined the intensity of the bad odor on a scale from 1 to 10 (1=not perceptible, to 10=extremely strong). A bad odor is produced by bacteria present in the washing machine and in the washing water, and brought in by the previously worn laundry.

In a further washing experiment (V2), 0.6 wt % (based on the total weight of the washing agent) of a silicic acid ester mixture of phenylethyl silicic acid ester, geranyl silicic acid ester, and citronellyl silicic acid ester was introduced in addition to the heavy-duty washing agent.

In a further washing experiment (V3), 0.6 wt % (based on the total weight of the washing agent) of a 1-aza-3,7-dioxabicyclo[3.3.0]octane compound of the general formula (I), with octanol as a corresponding scent alcohol, was introduced in addition to the heavy-duty washing agent.

In another further washing experiment (E1), 0.3 wt % of a silicic acid ester mixture of phenylethyl silicic acid ester, geranyl silicic acid ester, and citronellyl silicic acid ester and 0.3 wt % of a 1-aza-3,7-dioxabicyclo[3.3.0]octane compound of the general formula (I), with octanol as a corresponding scent alcohol, were introduced in addition to the heavy-duty washing agent.

The results are shown in Table 1.

TABLE 1

| | Intensity of bad odor | | | |
| --- | --- | --- | --- | --- |
| | V1 | V2 | V3 | E1 |
| Fresh | 2 | 2.2 | 2.4 | 2.3 |
| 1 day | 5.7 | 5.1 | 3.5 | 2.5 |
| 4 days | 8.4 | 7.6 | 4.5 | 2.6 |

The results show the appreciably improved performance of the combination according to the present invention in counteracting and covering bad odors resulting from bacteria and brought in by the previously worn laundry, in particular over a period of several days.

EXAMPLE 2

A textile made of cotton terrycloth had 100 mg of the "perspiration" bad odor (20 wt % octanoic acid, 20 wt % nonanoic acid, 20 wt % methylbutanoic acid, 20 wt % 2-ethyl-2-hexenoic acid, and 20 wt % 3-mercapto-1-hexanol) applied in non-exhaust fashion to it.

A household washing machine (Miele W1735) was then loaded with 3.5 kg accompanying laundry and with the treated fabric pieces. In addition, 75 ml of a liquid heavy-duty washing agent that contained 0.45 wt % perfume (based on the total liquid washing agent) was added. The laundry was washed at 40° C. and then left to sit for four days at 20° C. in the washer drum (V1).

Washing experiments were also carried out in which the following were introduced into the washing machine in addition to the heavy-duty washing agent:

(V2) 0.6 wt % of a silicic acid ester mixture of phenylethyl silicic acid ester, geranyl silicic acid ester, and citronellyl silicic acid ester, (V3) 0.6 wt % of a 1-aza-3,7-dioxabicyclo[3.3.0]octane compound of the general formula (I), with octanol as a corresponding scent aldehyde, (E1) 0.3 wt % of a silicic acid ester mixture of phenylethyl silicic acid ester, geranyl silicic acid ester, and citronellyl silicic acid ester and 0.3 wt % of a 1-aza-3,7-dioxabicyclo[3.3.0]octane compound of the general formula (I) with octanol as a corresponding scent alcoholaldehyde.

All weight indications are based on the total weight of the washing agent.

The results are shown in Table 2.

TABLE 2

| | Intensity of bad odor | | | |
| --- | --- | --- | --- | --- |
| | V1 | V2 | V3 | E1 |
| Fresh | 9.1 | 8.6 | 5.3 | 4.8 |
| 1 day | 7.3 | 7.0 | 3.2 | 2.4 |
| 4 days | 6.5 | 6.1 | 2.7 | 2.2 |

The results show the appreciably improved performance of the combination according to the present invention in counteracting and covering bad odors, especially perspiration odor, in particular over a period of several days.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A composition for providing the delayed release of scent comprising:

(a) a 1-aza-3,7-dioxabicyclo[3.3.0]octane compound of the general formula (I)

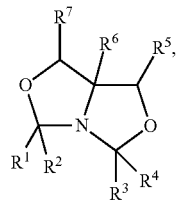

wherein
$R^1$, $R^2$, $R^3$, $R^4$ mutually independently denote residues that, in a compound of the general formula $R^1$—C(=O)—$R^2$ or $R^3$—C(=O)—$R^4$, yield a scent aldehyde having at least six carbon atoms or a scent ketone having at least six carbon atoms,
$R^5$, $R^6$, $R^7$ mutually independently denote H or a hydrocarbon residue that can be acyclic or cyclic, substituted or unsubstituted, branched or unbranched as well as saturated or unsaturated,
or mixtures of said compounds, and
(b) a silicic acid ester of the general formula (II)

$$R \left[ O - \underset{\underset{OR}{|}}{\overset{\overset{OR}{|}}{Si}} - OR \right]_n$$

wherein
n assumes values in the range from 2 to 100, and
all R are selected mutually independently from the group of hydrogen, straight-chain or branched, saturated or unsaturated, substituted or unsubstituted $C_{1-6}$ hydrocarbon residues and scent alcohol residues, with the provision that at least one R denotes a scent alcohol residue,
or mixtures of said compounds.

2. The composition according to claim 1, wherein $R^1$, $R^2$, $R^3$, $R^4$ mutually independently denote residues that, in a compound of the general formula $R^1$—C(=O)—$R^2$ or $R^3$—C(=O)—$R^4$, respectively yield a scent aldehyde having at least 6 carbon atoms.

3. The composition according to claim 1, wherein residues $R^1$ and $R^2$ or $R^3$ and $R^4$ that yield a scent ketone in a compound of the general formula $R^1$—C(=O)—$R^2$ or $R^3$—C(=O)—$R^4$, respectively, are present at most in one of the structural elements —$CR^1R^2$ or —$CR^3R^4$, respectively.

4. The composition according to claim 1, wherein in the compound of the general formula (I) the residues $R^1$, $R^2$, $R^3$ and $R^4$ yield, in a compound of the general formula $R^1$—C(=O)—$R^2$ or $R^3$—C(=O)—$R^4$, a scent aldehyde or a scent ketone that is selected from the list made up of jasmones; ionones, damascones and damascenones, menthone, carvone, Iso-E-Super, methylheptenone, melonal, cymal, ethylvanillin, helional, hydroxycitronellal, koavone, methyl nonyl acetaldehyde, phenylacetaldehyde, undecyleneadehyde, 3-dodecene-1-al, alpha-n-amylcinnamaldehyde, benzaldehyde, 3-(4-tert-butylphenyl)propanal, 2-methyl-3-(para-methoxyphenylpropanal), 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropyl-benzyldehyde, 2,4-dimethyl-3-cyclohexene-1-carboxyaldehyde, 2-methyl-3-(isopropylphenyl)propanal, decylaldehyde, 2,6-dimethyl-5-heptenal, alpha-n-hexylcinnamaldehyde, 7-hydroxy-3,7-dimethyloctanal, undecenal, 2,4,6-trimethyl-3-cyclohexene-1-carboxaldehyde, 1-dodecanal, 2,4-dimethylcyclohexene-3-carboxaldehyde, 4-(4-hydroxy-4-methylpentyl)-3-cylohexene-1-carboxaldehyde, 2-methylundecanal, 2-methyldecanal, 1-nonanal, 1-octanal, 2,6,10-trimethyl-5,9-undecadienal, 2-methyl-3-(4-tertbutyl)propanal, dihydrocinnamaldehyde, 3,7-dimethyloctan-1-al, 1-undecanal, 10-undecen-1-al, 4-hydroxy-3-methoxybenzaldehyde, trans-4-decenal, 2,6-nonadienal, para-tolylacetaldehyde, 3,7-dimethyl-2-methylene-6-octenal, 2-methyloctanal, alpha-methyl-4-(1-methylethyl)benzeneacetaldehyde, 2-methyl-3-phenyl-2-propen-1-al, 3,5,5-trimethylhexanal, 3-propylbicyclo[2.2.1]hept-5-ene-2-carbaldehyde, 9-decenal, 3-methyl-5-phenyl-1-pentanal, methylnonylacetaldehyde, citral, 1-decanal, florhydral, 2,4-dimethyl-3-cyclohexene-1-carboxaldehyde, heliotropin.

5. The composition according to claim 1, wherein in the silicic acid ester of the general formula (II) at least 10 mol %, preferably at least 20 mol % and particularly preferably even more than 40 mol % of the residues R are selected from the group of the residues of the following scent alcohols: 10-undecen-1-ol, 2,6-dimethylheptan-2-ol, 2-methylbutanol, 2-methylpentanol, 2-phenoxyethanol, 2-phenylpropanol, 2-tert-butylcyclohexanol, 3,5,5-trimethylcyclohexanol, 3-hexanol, 3-methyl-5-phenylpentanol, 3-octanol, 3-phenylpropanol, 4-heptenol, 4-isopropylcyclohexanol, 4-tert-butylcyclohexanol, 6,8-dimethyl-2-nonanol, 6-nonen-1-ol, 9-decen-1-ol, α-methylbenzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethylbenzylcarbinol, dimethylheptanol, dimethyloctanol, ethyl salicylate, ethylvanillin, eugenol, farnesol, geraniol, heptanol, hexyl salicylate, isoborneol, isoeugenol, isopulegol, linalool, menthol, myrtenol, n-hexanol, nerol, nonanol, octanol, p-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, championiol, hexenol, and/or cinnamyl alcohol.

6. A composition for providing the delayed release of scent comprising a mixture of a combination of compounds of the general formulas (I) and (II) according to claim 1 and compounds of the general formula (III)

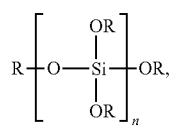

having the meanings for $R^1$, $R^2$, $R^5$, $R^6$, $R^7$ indicated in the general formula (I).

7. A washing or cleaning agent, fabric softener, or cosmetic comprising the composition according to claim 6, wherein the composition comprising the compound of the general formula (I), (II) and/or (III) or mixtures thereof, are contained in the agent in quantities of less than 5 wt %, based in each case on the total quantity of the agents.

8. A washing or cleaning agent, fabric softener, or cosmetic comprising the composition according to claim 1.

9. A method for extending the scent sensation of a washing or cleaning agent, fabric softener, or cosmetic, or of solid surfaces treated therewith, wherein a composition according to claim 1 is added to the washing or cleaning agent, fabric softener, or cosmetic.

10. A method for degrading bad odors, comprising: applying to a surface a composition a composition including:
 (a) a 1-aza-3,7-dioxabicyclo[3.3.0]octane compound of the general formula (I)

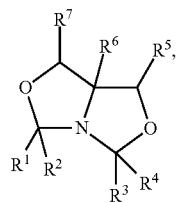
(I)

wherein $R^1$, $R^2$, $R^3$, $R^4$ mutually independently denote residues that, in a compound of the general formula $R^1$—C(=O)—$R^2$ or $R^3$—C(=O)—$R^4$, yield a scent aldehyde having at least six carbon atoms or a scent ketone having at least six carbon atoms, $R^5$, $R^6$, $R^7$ mutually independently denote H or a hydrocarbon residue that can be acyclic or cyclic, substituted or unsubstituted, branched or unbranched as well as saturated or unsaturated, or mixtures of said compounds, and (b) a silicic acid ester of the general formula (II)

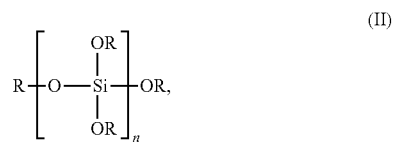
(II)

wherein n assumes values in the range from 2 to 100, and all R are selected mutually independently from the group of hydrogen, straight-chain or branched, saturated or unsaturated, substituted or unsubstituted $C_{1-6}$ hydrocarbon residues and scent alcohol residues, with the provision that at least one R denotes a scent alcohol residue, or mixtures of said compounds.

11. The method of claim 10, wherein the surface is a textile.

12. The method of claim 10, wherein the surface is a hard surface.

13. The method of claim 10, wherein the applying is accomplished by spraying.

* * * * *